(12) United States Patent
Eleniak

(10) Patent No.: US 9,884,154 B2
(45) Date of Patent: Feb. 6, 2018

(54) MEDICATION INJECTING APPARATUS

(71) Applicant: Darcy Eleniak, Leduc (CA)

(72) Inventor: Darcy Eleniak, Leduc (CA)

(*) Notice: Subject to any disclaimer, the term of this patent is extended or adjusted under 35 U.S.C. 154(b) by 108 days.

(21) Appl. No.: 15/194,846

(22) Filed: Jun. 28, 2016

(65) Prior Publication Data

US 2017/0368266 A1   Dec. 28, 2017

(51) Int. Cl.
| | | |
|---|---|---|
| A61M 5/00 | (2006.01) | |
| A61M 5/315 | (2006.01) | |
| A61M 5/24 | (2006.01) | |
| A61M 5/31 | (2006.01) | |

(52) U.S. Cl.
CPC ...... *A61M 5/31585* (2013.01); *A61M 5/2459* (2013.01); *A61M 5/31526* (2013.01); *A61M 5/31536* (2013.01); *A61M 5/31551* (2013.01); *A61M 5/31568* (2013.01); *A61M 2005/3126* (2013.01)

(58) Field of Classification Search
CPC .. A61M 2005/2407; A61M 2005/2488; A61M 5/24; A61M 5/31541; A61M 5/31551; A61M 5/31585
See application file for complete search history.

(56) References Cited

U.S. PATENT DOCUMENTS

| | | | |
|---|---|---|---|
| 5,244,465 A * | 9/1993 | Michel | A61M 5/24 604/187 |
| 6,537,251 B2 | 3/2003 | Klitmose | |
| 6,796,970 B1 | 9/2004 | Klitmose et al. | |
| 7,220,248 B2 | 5/2007 | Mernoe | |
| 7,291,132 B2 | 11/2007 | DeRuntz et al. | |
| 8,361,028 B2 | 1/2013 | Gross et al. | |
| 8,632,519 B2 | 1/2014 | Lum et al. | |
| 9,022,988 B1 | 5/2015 | Shaban | |
| 9,220,843 B2 | 12/2015 | Mudd | |
| 2014/0094754 A1 | 4/2014 | Servansky | |
| 2014/0276431 A1 | 9/2014 | Estes et al. | |
| 2014/0303566 A1* | 10/2014 | Stever | A61M 5/31501 604/220 |

* cited by examiner

*Primary Examiner* — Rebecca E Eisenberg
(74) *Attorney, Agent, or Firm* — Lewellyn Law, PLLC; Stephen Lewellyn

(57) ABSTRACT

A medication injecting apparatus has a cartridge housing and a drive housing that is threadedly connected to the cartridge housing for axial displacement relative to one another. The drive housing has a helical-shaped passage and a flexible drive member is slidingly disposed within the helical-shaped passage and extends axially outwardly therefrom toward the cartridge housing. The flexible drive member is movable in the axial direction relative to the drive housing during dose setting and is axially fixed relative to the drive housing during injecting. A clutch has an engaged position and a disengaged position. The flexible drive member is axially fixed relative to the drive housing when the clutch is in the engaged position and the flexible drive member is movable relative to the drive housing when the clutch is in the disengaged position.

11 Claims, 4 Drawing Sheets

MEDICATION INJECTING APPARATUS

FIELD OF THE INVENTION

The present invention relates generally to medication injecting, and more particularly, relating to a medication dispensing apparatus in the form of a portable injector pen.

BACKGROUND OF THE INVENTION

Medication dispensing devices in the form of injector pens are known. One such injector pen construction is described in U.S. Pat. No. 7,291,132, which is incorporated herein in its entirety by reference. While the injector pens heretofore fulfill their respective, particular objectives and requirements, they do have drawbacks. For instance, the devices heretofore have complex constructions that are bulky and difficult to operate. As such there exists and need for an injector pen having a compact construction that is easy to operate.

SUMMARY OF THE INVENTION

Embodiments of the present invention provide a medication injecting device that has a compact, axial construction that is simple to operate. The compact axial construction provides a shorter axial length that is easier to store and transport.

In general, in one aspect, a medication injecting apparatus has a cartridge housing and a drive housing that is threadedly connected to the cartridge housing for axial displacement relative to one another. The drive housing has a helical-shaped passage and a flexible drive member is slidingly disposed within the helical-shaped passage and extends axially outwardly therefrom toward the cartridge housing. The flexible drive member is movable in the axial direction relative to the drive housing during dose setting and is axially fixed relative to the drive housing during injecting.

There has thus been outlined, rather broadly, the more important features of the invention in order that the detailed description thereof that follows may be better understood and in order that the present contribution to the art may be better appreciated.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

For a better understanding of the invention, its operating advantages and the specific objects attained by its uses, reference should be had to the accompanying drawings and descriptive matter in which there are illustrated embodiments of the invention.

BRIEF DESCRIPTION OF THE DRAWINGS

The following drawings illustrate by way of example and are included to provide further understanding of the invention for the purpose of illustrative discussion of the embodiments of the invention. No attempt is made to show structural details of the embodiments in more detail than is necessary for a fundamental understanding of the invention, the description taken with the drawings making apparent to those skilled in the art how the several forms of the invention may be embodied in practice. Identical reference numerals do not necessarily indicate an identical structure. Rather, the same reference numeral may be used to indicate a similar feature of a feature with similar functionality. In the drawings.

DETAILED DESCRIPTION OF THE INVENTION

Figure 1:
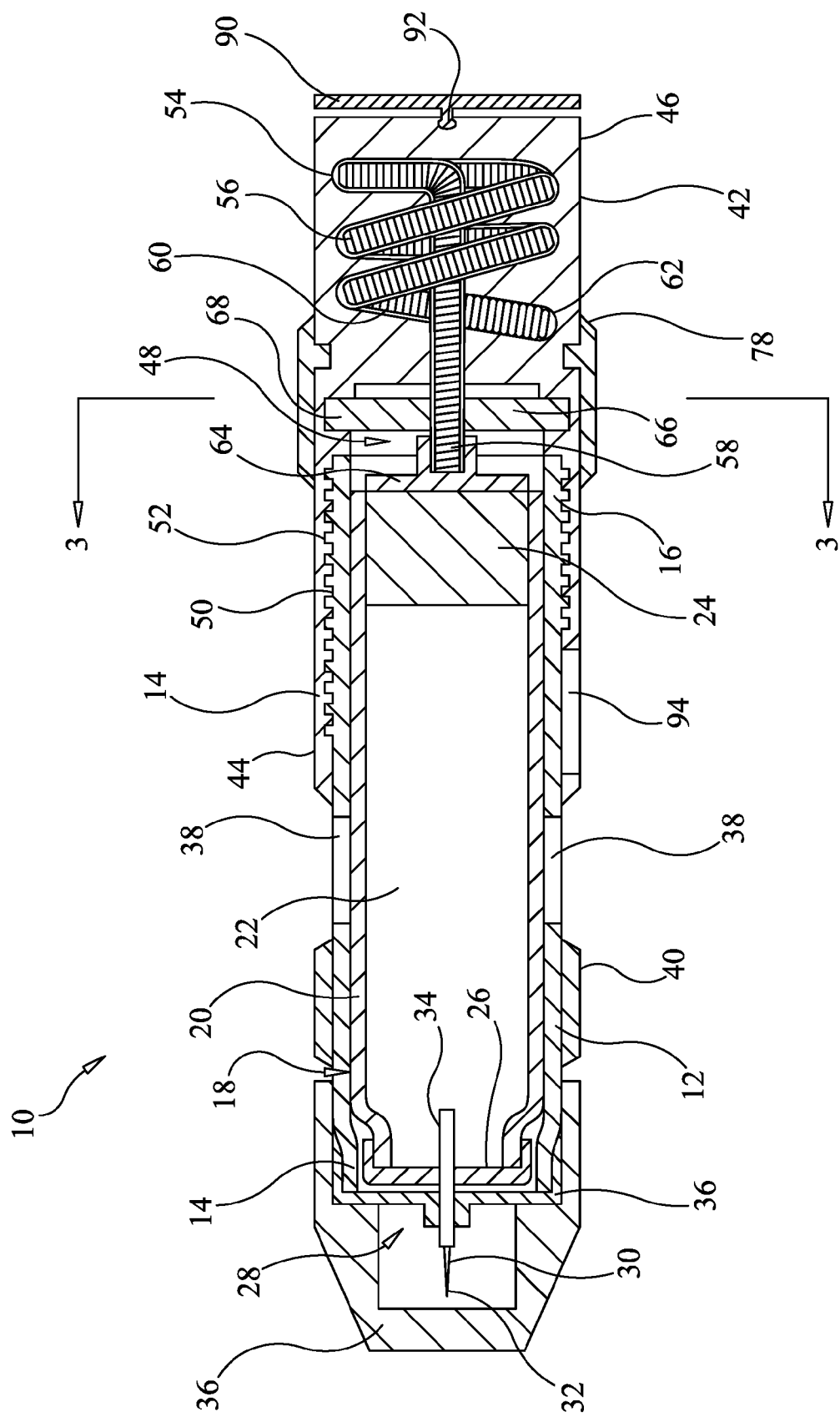
FIG. 1 is a side view in longitudinal cross-section of a medication dispensing apparatus that is construction accordance with the principles of the present invention, showing the apparatus in a first position, non-extended position.

With reference to FIGS. 1-4, there is representatively illustrated a medication injecting apparatus 10 that is constructed in accordance with an embodiment of the present invention. Any directional references in this description, such as right or left, upper or lower, or clockwise or counterclockwise, are intended for convenience of the description, and by itself does not limit the present invention or any of its components to any particular position or spatial orientation.

In the depicted embodiment, the apparatus 10 is shown as an injector pen having an elongated form. In addition, in the depicted embodiment, injector pen 10 is a reusable injector pen that may be reloaded with a new cartridge after exhausting a previous cartridge by multiple operations of the injector pen. In other embodiments, the injector pen 10 could be a disposable pen or prefilled pen that is discarded after exhausting the prefilled medication. As will become apparent from the description below, injector pen 10 is operated to deliver a dose in a specific amount and is then reset for additional dosing.

Injector pen 10 has a cartridge housing 12 having distal end 14, a proximal end 16 and defines an interior receptacle 18 that extends between the distal and proximal ends. A cartridge 20 is removably disposed within receptacle 18 though proximal end 16 of the cartridge housing 12. Cartridge 20 is of a conventional construction and has a medicine-filled reservoir 22 that is closed at its proximal end by a piston 24. Piston 24 is axially slidable and sealingly engaged with the cartridge interior wall to hold the fluid medication contained within reservoir 22. The distal, outlet end of the cartridge reservoir 22 is sealed by a septum 26.

A needle assembly 28 is of a known design and includes a double-ended needle cannula 30 having a distal tip 32 at one end and a proximal point 34 at the other. The needle 30 is mounted in a tubular hub 36 that has internal threading to cooperate with the distal end 14 of the cartridge housing 12 so as to be removably attached to the distal end. When attached to the distal end 14 of the cartridge housing 12, the proximal point 34 of the needle 30 penetrates cartridge septum 26 to provide a fluid flow outlet by which medicine within cartridge reservoir 22 can be dispensed from needle tip 32 during operation of the pen injector 10. A protective cap 36 is removably attached to the distal end 14 of the cartridge housing 12 and encloses the needle 30. The protective cap 36 is removed from cartridge housing 12 during operation of the pen injector 10.

Cartridge housing 12 includes one or more slots 38 that are formed through and spaced circumferentially around the sidewall of the housing. Slots 38 allow the contents of the cartridge to be seen to let a user estimate the medicine remaining and to help removing the cartridge from receptacle 18.

A soft-touch grip 40 is disposed on the exterior of the cartridge housing sidewall and provides a user with a comfortable, slip-free grip of the injector pen 10 when operating the injector pen.

With continued reference to FIGS. 1-4, the pen injector 10 further includes a drive housing 42 having distal end 44 and a proximal end 46. The distal end 44 defines an interior hollow 48 into which the proximal end 16 of the cartridge housing is received. The interior hollow 48 has a cylindrical interior surface having helical threading 50 along a portion of its axial length that engages a corresponding threading 52 formed on the exterior surface of the proximal end 16 of the cartridge housing 12 to threadedly connect the cartridge housing and the drive housing 42. Threads 50 and 52 are non-binding to facilitate backdriving when an axial force is applied to the drive housing 42.

The proximal end 46 of the drive housing 42 defines a helical-shaped, blind passage 54 that opens to the interior hollow 48 of the distal end 44 of the drive housing. A flexible drive member 56 in the form of an elongated, compressed helical spring of fine gage spring material is slidingly disposed within passage 54. The drive member 56 has a distal end 58 and a proximal end 60. The distal end 58 of the drive member 56 extends from passage 54 in an axial direction into the interior hollow 48 and the proximal end 60 terminates within passage 54. As shown, the drive member 56 that is slidingly disposed in passage 54 bends and conforms to the helical-shape of the passage and the portion of the drive member that extends axially from the passage and into the interior hollow 48 is substantially straight. The drive member 56 is spring biased in a direction outwardly from the passage 54 by a spring 62 that is disposed within passage 54 between the proximal end 60 of the drive member and the terminal end of the passage. The helical-shaped passaged 54 and the flexible drive member 56 provide the advantage of having a drive member of a linear length required for dose setting and dose injection and having a compact construction wherein the linear length of the drive member is contained along an axial length of the injector pen 10 that is much less than the axial length of the drive member.

A disc-shaped foot 64 is rotatable attached and axially fixed to the distal end 58 of the drive member 56. The foot 64 contacts and directly engages the cartridge piston 24 during piston advancing by the drive member 56 when operating the injector pen 10, which is explained in further detail below.

Figure 3:
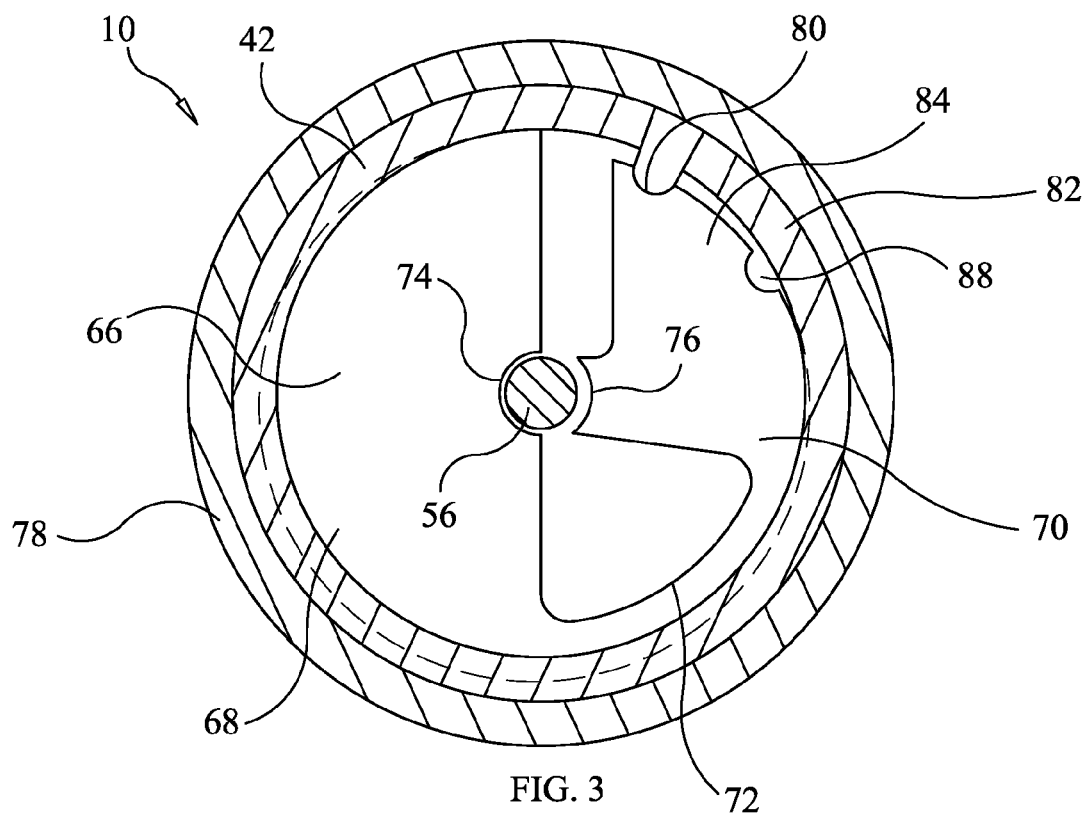
FIG. 3 is a cross-sectional view of the medication dispensing apparatus taken along line 3-3 in FIG. 1, showing a clutch in a first, non-engaged position.
Figure 4:
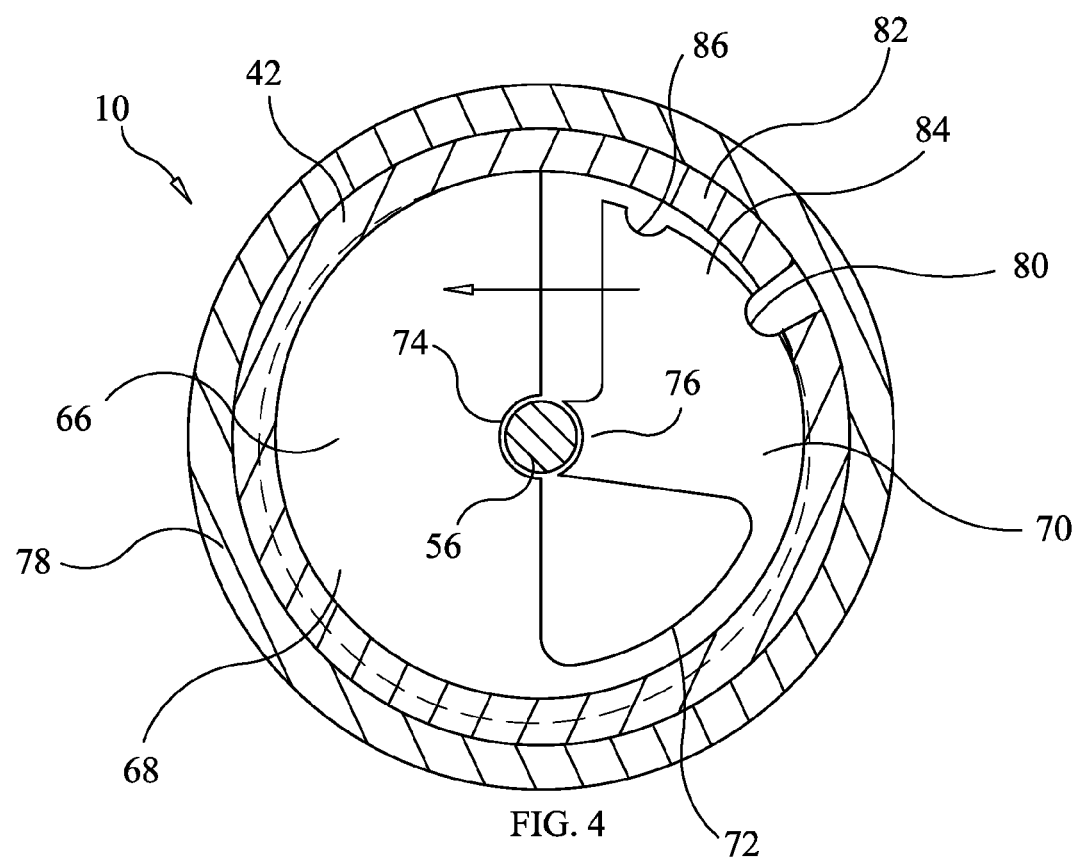
FIG. 4 is a cross-section view of the medication dispensing apparatus taken along line 4-4 in FIG. 2, showing a clutch in a second, engaged position.
Figure 5:
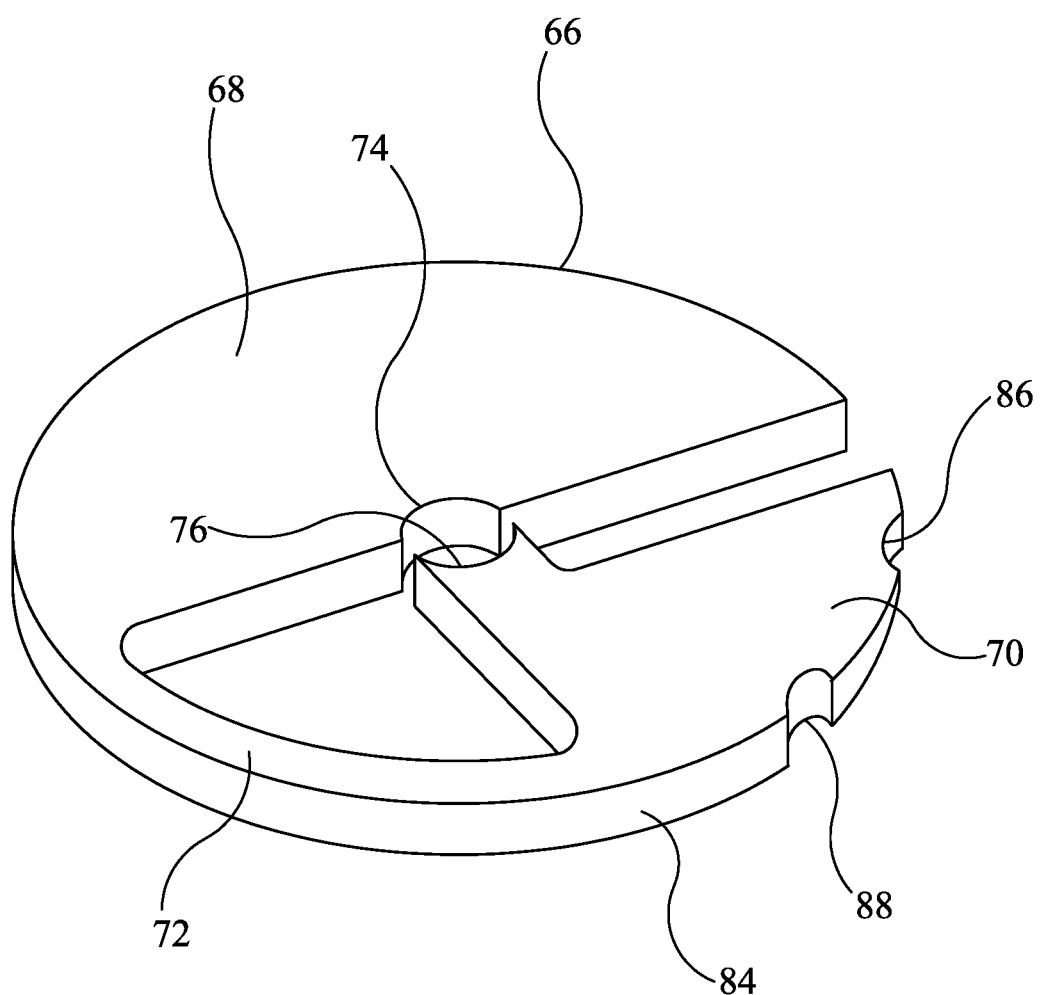
FIG. 5 is a perspective view of a clutch.

A clutch 66 in the form of a disc is disposed within and extends across the interior hollow 48 at a position proximal to the foot 64 and is received and retained by a groove 68 formed circumferentially around the interior wall surface of the interior hollow. The drive member 56 extends through the clutch 66. More specifically, as best seen in FIGS. 3-5, the clutch 66 includes a fixed portion 68 and a tab portion 70 that is connected to the fixed portion by spring finger 72. The fixed portion 68 of the clutch defines a semi-circular passage 74 and the tab portion 70 defines a corresponding semi-circular passage 76. The drive member 56 extends through and between the semi-circular passages 74 and 76.

The tab portion 70 is movable toward and away from the fixed portion 68 between a first position where semi-circular passage 76 is positioned away from semi-circular passage 74 (FIG. 3) and a second position where the semi-circular passage 76 is positioned toward semi-circular passage 74 (FIG. 4). When the tab portion 70 is in the first position, the drive member 56 is permitted to freely pass back-and-forth through and between the semi-circular passages 74 and 76 of the clutch 66. When the tab portion 70 is in the second position, the drive member 56 is grasped by and between the semi-circular passages 74 and 76 so that the drive member is held in a fixed axial position by the clutch 66 and in turn is axially fixed relative to the drive housing 42.

A collar 78 encircles and is rotatably connected to and extends along an axial length of the exterior sidewall of the drive housing 42 for rotation about the drive housing between a first position (FIG. 3) and a second position (FIG. 4). A detent 80 extends from the interior surface of the collar 78 in a direction inwardly of the drive housing 42 and through a circumferential slot 82 formed through the sidewall of the drive housing. The detent 80 slidingly contacts a circumferential edge 84 of the tab portion 72 of clutch 66. The circumferential edge 84 of the tab portion 72 tapers toward the interior surface of the interior hollow 48 in a counterclockwise direction. To this end, when the collar 78 is in the first position, seen in FIG. 3, the tab portion 70 is in its first position. When collar 78 is rotated from the first position and into the second position, seen in FIG. 4, the detent 80 slides along the tapering edge 84, causing the tab portion to be urged inwardly into its second position where the drive member 56 becomes engaged and fixedly held by the clutch 66.

Collar 78 is restrained from movement between its first and second positions by the detent being received by notches 86 and 88, respectively. In addition, collar 78 is prevented from over rotating by the detent 80 contacting the opposite side edges of slot 82 when the collar is rotated between its first and second positions. The exterior surface of the collar 78 may be knurled or otherwise formed to facilitate being gripped by a user's fingers.

A button 90 is rotatably attached and axially fixed to the proximal end 46 of the drive housing 42 by stem 92 being captively and rotatably received by the proximal end of the drive housing. During operation of the injector pen 10, button 90 permits a user to apply axial force against the proximal end 46, such as by pressing a finger against the button to advance the drive member 56 axially, while allowing the drive housing 42 to rotate.

Figure 2:
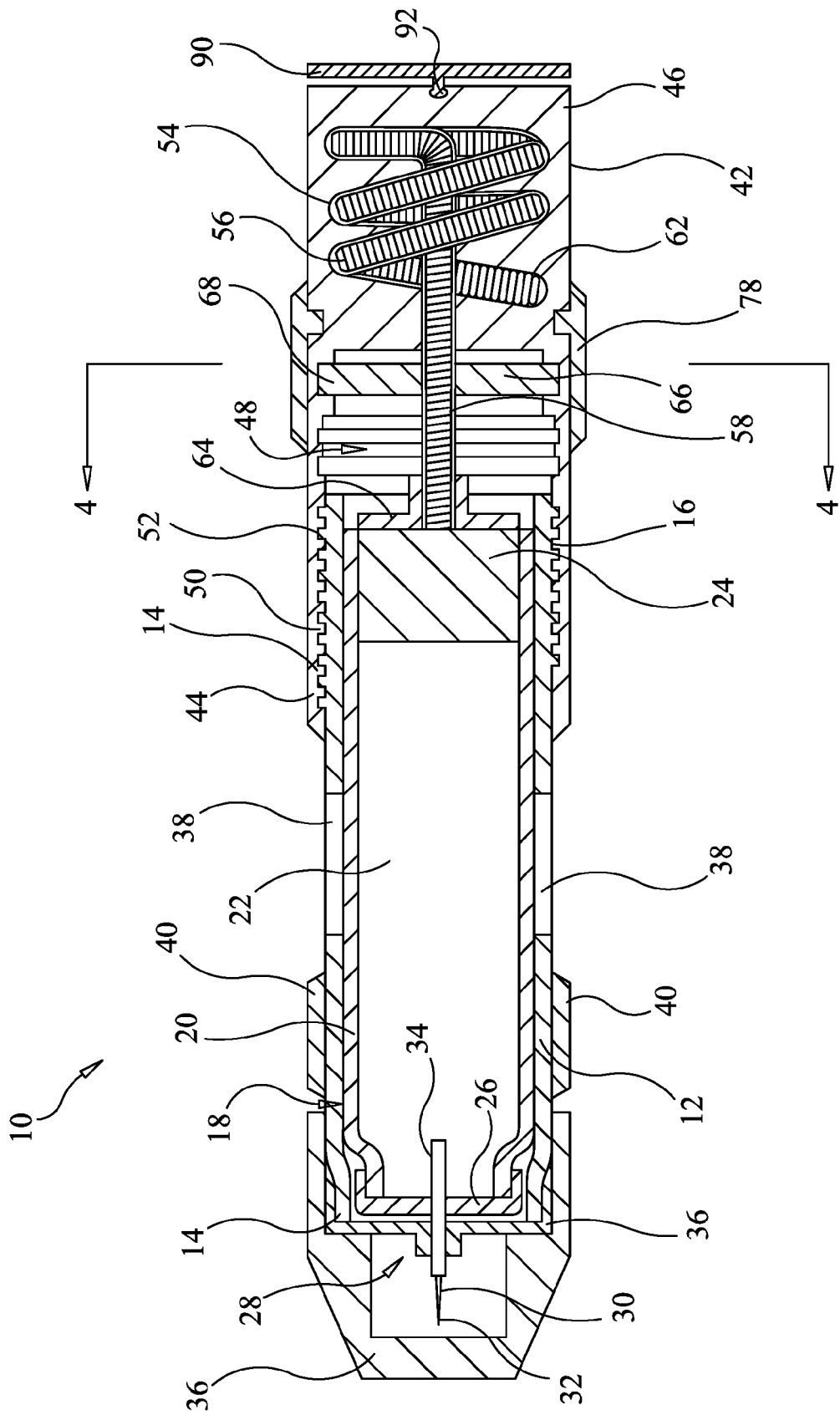
FIG. 2 is a side view in longitudinal cross-section of the medication dispensing apparatus of FIG. 1, shown in a second, extending and dosing ready position.

Injector pen 10 allows a user to select a delivery dose of medication from the cartridge 20 by rotating the drive housing 42 relative to the cartridge housing 12 from a position shown in FIG. 1 to a position shown in FIG. 2 where the drive housing and cartridge housing are axially displaced in an outwardly direction, thereby extending the length of the injector pen 10 a distance equal to a desire dose amount. To facilitate setting a dose, dosing marks are provided in the form of a helically arranged pattern of lines, numerals, or other indicia on the exterior surface of the cartridge housing 12, which are visible through window 94 formed through the distal end 44 of the drive housing 42. Detents or other stop structures may be provided between the cartridge housing 12 and the drive housing 42 to provide a stop-type rotation between the two housings corresponding to the dosing marks.

To inject a dose from the injector pen 10, the clutch 66 is positioned in its first, disengaged position, as seen in FIG. 3, by rotating collar 78 in a counterclockwise direction relative to the perspective view of FIG. 3. The drive housing 42 is then turned relative to the cartridge housing 12 by an incremental rotation to axially move the housings away from one another a distance corresponding to a desired dose as provided by the dosing marks. This rotation positions the injector pen 10 from a non-dosing position (FIG. 1) into a dosing position (FIG. 2). When moved into the dosing position, the drive member 56 is urged in an outwardly direction from passage 54 by spring 62, thereby retaining contact between foot 66 and cartridge piston 24. The force provided by spring 62 is sufficient to urge the drive member 56 from passage 54, but is insufficient to overcome the frictional force between the cartridge piston 24 and the interior wall of the cartridge 20, and therefore is unable to move the piston.

Once the dose has been set, the clutch 66 is moved into its second position, as seen in FIG. 4, by rotating collar 78 in a clockwise direction relative to the perspective view of FIG. 4. As discussed above, in the engaged position, clutch 66 engages drive member 56 and axially fixes the drive member relative to the drive housing 42 so as to be conjointly moved axially with the drive housing. After clutch 66 is engaged, the injector pen 10 is positioned so that the injection needle tip 32 penetrates a user's skin and then an axial force is applied to the button 90 to backdrive the drive housing 42 relative to the cartridge housing 12 to force the drive member 56, via foot 66, against cartridge piston 24 to dispense medicine from the cartridge 20 through needle 30.

A number of embodiments of the present invention have been described. Nevertheless, it will be understood that various modifications may be made without departing from the spirit and scope of the invention. Accordingly, other embodiments are within the scope of the following claims.

What is claimed is:

1. A medication injecting apparatus comprising:
a cartridge housing;
a drive housing threadedly connected to said cartridge housing for axial displacement relative to one another, said drive housing having a helical-shaped passage;
a flexible drive member slidingly disposed within said helical-shaped passage and extending axially outwardly therefrom toward said cartridge housing; and
said flexible drive member movable in the axial direction relative to said drive housing during dose setting and axially fixed relative to said drive housing during injecting.

2. The medication injecting apparatus of claim 1 further comprising:
a clutch having an engaged position and a disengaged position, said flexible drive member to axially fixed relative to said drive housing when said clutch is in said engaged position, and said flexible drive member movable relative to said drive housing when said clutch is in said disengaged position.

3. The medication injecting apparatus of claim 1, wherein said flexible drive member is a helical spring.

4. A medication injecting apparatus comprising:
a cartridge housing having a cartridge housing distal end, a cartridge housing proximal end, and an interior receptacle that extends between said cartridge housing distal end and said cartridge housing proximal end;
a cartridge disposed within said receptacle and having a medicine-filled reservoir with a movable piston at one end and an outlet at the other end that is positioned at said cartridge housing distal end;
a drive housing having a drive housing distal end, a drive housing proximal end, an interior hollow defined by said drive housing distal end, and a helical-shaped passage defined by said proximal end, said helical-shaped passage opening into said interior hollow;
a flexible drive member having a drive member distal end and a drive member proximal end, said flexible drive member slidingly disposed within said helical-shaped passage and extending axially outwardly therefrom into said interior hollow, said drive member distal end disposed within said interior hollow and said drive member proximal end disposed within said helical-shaped passage, said flexible drive member biased in a direction outwardly from said helical-shaped passage;
said flexible drive member movable in the axial direction relative to said drive housing during dose setting and axially fixed relative to said drive housing during injecting;
a foot rotatably attached and axially fixed to said distal end of said flexible drive member, said foot contacting said piston; and
said drive housing threadedly connected to said cartridge housing for axial displacement relative to one another.

5. The medication injecting apparatus of claim 4, further comprising:
a clutch having an engaged position and a disengaged position, said flexible drive member to axially fixed relative to said drive housing when said clutch is in said engaged position, and said flexible drive member movable relative to said drive housing when said clutch is in said disengaged position.

6. The medication injecting apparatus of claim 4, wherein said flexible drive member is a helical spring.

7. The medication injecting apparatus of claim 4, further comprising:
a spring disposed within said helical-shaped passage between said proximal end of said flexible drive member and an end of said helical-shaped passage, said spring biasing said flexible drive member outwardly from said helical-shaped passage.

8. The medication injecting apparatus of claim 4, wherein said cartridge housing includes slots formed through a sidewall thereof.

9. The medication injecting apparatus of claim 4, further comprising:
a button rotatably attached and axially fixed to said proximal end of said drive housing.

10. The medication injecting apparatus of claim 4, further comprising:
a grip disposed on the exterior of the cartridge housing sidewall.

11. The medication injecting apparatus of claim 4, further comprising:
- first helical threads on a cylindrical interior surface of said interior hollow;
- second helical threads on the exterior surface of said proximal end of said cartridge housing;
- said first and second helical threads providing said threaded connection between said drive housing and said cartridge housing; and
- said first and second helical threads being back-drivable.

* * * * *